United States Patent [19]

Handte et al.

[11] 4,431,813

[45] Feb. 14, 1984

[54] PROCESS FOR THE PREPARATION OF 2-MERCAPTOBENZOTHIAZOLES

[75] Inventors: Reinhard Handte, Hofheim am Taunus; Lothar Willms, Unkel; Ernst Blume, Bad Soden am Taunus, all of Fed. Rep. of Germany

[73] Assignee: Hoechst A.G., Frankfurt am Main, Fed. Rep. of Germany

[21] Appl. No.: 239,445

[22] Filed: Mar. 2, 1981

[30] Foreign Application Priority Data

Mar. 4, 1980 [DE] Fed. Rep. of Germany ....... 3008225

[51] Int. Cl.$^3$ ........................................... C07D 277/72
[52] U.S. Cl. ................................................... 548/165
[58] Field of Search ......................................... 548/165

[56] References Cited

U.S. PATENT DOCUMENTS

| 1,631,871 | 6/1927 | Kelly | 548/175 |
| 1,785,656 | 12/1930 | Sebrell et al. | 548/175 |
| 2,001,587 | 5/1935 | Semar | 548/175 |

*Primary Examiner*—Paul M. Coughlan, Jr.
*Assistant Examiner*—D. B. Springer
*Attorney, Agent, or Firm*—Curtis, Morris & Safford

[57] ABSTRACT

The preparation of (optionally substituted) 2-mercaptobenzothiazole by reaction of corresponding 2-halogenoanilines with an alkali metal xanthate or alkaline earth metal xanthate or with $CS_2$ in the presence of bases.

6 Claims, No Drawings

PROCESS FOR THE PREPARATION OF 2-MERCAPTOBENZOTHIAZOLES

Various processes for the preparation of 2-mercaptobenzothiazoles are described in the literature, the preparation of unsubstituted 2-mercaptobenzothiazole, in particular, being the subject of a large number of patent applications and publications.

The most important preparation processes are based on the reaction of 2-chloronitrobenzene with hydrogen sulfide and carbon disulfide, or on the reaction of aniline with sulfur and carbon disulfide (for example Ullmanns Enzyklopädie der technischen Chemie (Ullmann's Encyclopaedia of Industrial Chemistry), 3rd edition, Volume 12, page 304; and Dutch Laid-Open Specification No. 78/00,037, Japanese Pat. No. 53,009-766, Italian Patent Specification No. 2,454,277, Dutch Laid-Open Specification No. 71/05,735, Japanese Pat. No. 71/21,019, Japanese Pat. No. 71/21,018, U.S. Pat. No. 674,091, U.S. Pat. No. 674,092, U.S. Pat. No. 674,093, German Offenlegungsschrift No. 2,709,989, U.S. Pat. No. 1,662,015, U.S. Pat. No. 1,785,656, U.S. Pat. No. 1,669,630 and U.S. Pat. No. 1,960,205). German Offenlegungsschrift No. 2,816,503 proposes the reaction of nitrobenzene in the presence of hydrogen sulfide and carbon disulfide for the preparation of 2-mercaptobenzothiazole. According to British Patent Nos. 1,379,127, 1,386,446 and 1,404,954, N-methylaniline or aniline can be reacted with dimethylformamide, and aniline can be reacted with an aliphatic amine, in each case in the presence of sulfur, to give 2-mercaptobenzothiazole. In the latter processes mentioned, the carbon disulfide necessary for the cyclization is formed as an intermediate.

The publications mentioned relate almost without exception to the preparation of unsubstituted 2-mercaptobenzothiazole. The preparation of a number of substituted 2-mercaptobenzothiazole is described, for example, in J. Am. Chem. Soc. 49,1748–58 and 1779–85 (1927), and 56, 2734–36 (1934). According to the earlier publications, substituted 2-chloronitrobenzenes, inter alia, are converted into the corresponding 2-mercaptobenzothiazoles by means of NaSH, $H_2S$ and $CS_2$; according to the latter literature reference mentioned, this reaction is effected by means of sodium sulfide, sulfur and carbon disulfide.

The primary step of this reaction most likely comprises replacement of the chlorine atom which is activated by the adjacent $NO_2$ group with sulfur, a —S—S— bridge being formed between two molecules of nitrobenzene. In a further step, the nitro group and the disulfide bridge are then reduced by means of sodium polysulfide (of $Na_2S+S$), and, finally, the 2-mercaptobenzothiazoles are formed from the resulting α-amino-thiophenols and $CS_2$.

One of the disadvantages of this procedure is the unfavorable proportions required, since large excesses of sodium sulfide, sulfur and carbon disulfide are used and large amounts of starting substances which have not been consumed remain. Above all, however, the process is unsuitable for the synthesis of 6-halogenomercaptobenzothiazoles, since only undefinable products are formed in the reaction with 2,4-dichloronitrobenzene.

Only one process for the preparation of 6-chloro- or 6-bromo-2-mercaptobenzothiazole is known in the literature. Teppema and Sebrell (J. Am. Chem. Soc. 49, 1783 (1927)) diazotized 6-amino-2-mercaptobenzothiazole (which had in turn been obtained by nitration of 2-mercaptobenzothiazole and subsequent reduction), and reacted the diazonium salt with copper-I chloride. According to Chem. Zvest, 27, 698–702 (1973), the corresponding bromine derivative is obtained if copper-I bromide is used, under the same conditions. However, the preparation of the compounds by this route is troublesome, and unsatisfactory from an industrial point of view, since the yields and the resulting purities are inadequate. Attempts to prepare 6-chloro-2-mercaptobenzothiazole by chlorination of the nucleus of 2-mercaptobenzothiazole were unsuccessful (J. Am. Chem. Soc. 49, 1783 (1927); see also German Pat. No. 1,168,911).

The present invention thus relates to a novel process for the preparation of 2-mercaptobenzothiazoles, which comprises reacting 2-halogenoanilines with alkali metal xanthates or alkaline earth metal xanthates, or with carbon disulfide, in the latter case in the presence of bases.

In principle, all the known monosubstituted or polysubstituted 2-mercaptobenzothiazoles can be prepared by the process according to the invention provided the radicals are inert towards the reaction medium under the reaction conditions used and do not cause steric hindrance. Thus, in the formula I

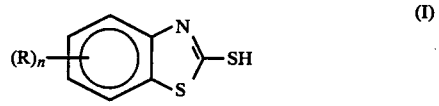
(I)

R can denote, for example, $(C_1-C_4)$alkyl, $(C_1-C_4)$alkoxy, $(C_1-C_4)$alkylthio, halogen (F, Cl, Br or I), halogeno $(C_1-C_4)$alkyl $(CF_3)$, halogeno$(C_1-C_4)$alkoxy, phenoxy, phenylthio, benzyl, benzyloxy (it being possible for the phenyl radicals to be substituted with halogen or lower alkyl), $NO_2$, OH, CN, di$(C_1-C_4)$alkylamino or lower alkoxy-, phenoxy-, halogeno- or alkyl-phenoxy-, alkylamino-, dialkylamino- or heteroamino-sulfonyl and n can denote 0 or a number from 1 to 4. The process is preferably used for the preparation of 6-chloro- and 6-bromo-2-mercaptobenzothiazoles, which were not previously directly obtainable.

The following compounds, for example, can be prepared by the process according to the invention (compare also the process examples): 4,6-dichloro-2-mercaptobenzothiazole, 7-chloro-2-mercaptobenzothiazole, 6-ethyl-2-mercaptobenzothiazole, 6-trifluoromethyl-2-mercaptobenzothiazole, 6-tert.-butyl-2-mercaptobenzothiazole, 6-methoxy-2-mercaptobenzothiazole, 6-ethoxy-2-mercaptobenzothiazole, 5-ethoxy-2-mercaptobenzothiazole, 5-fluoro-2-mercaptobenzothiazole, 5-bromo-2-mercaptobenzothiazole, 4-chloro-2-mercaptobenzothiazole, 6-nitro-2-mercaptobenzothiazole, 6-cyano-2-mercaptobenzothiazole, 6-phenoxy-2-mercaptobenzothiazole, 5-(4-dimethylaminosulfonyl)-2-mercaptobenzothiazole, 5-(4-methoxysulfonyl)-2-mercaptobenzothiazole and 5-(4-chlorophenoxysulfonyl)-2-mercaptobenzothiazole.

The process proceeds according to the following equation:

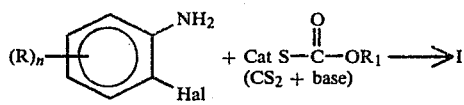

In the above equation, $(R)_n$ has the meaning given, Hal represents halogen, preferably fluorine, chlorine or bromine, and Cat represents an alkali metal cation or alkaline earth metal cation; $R_1$ denotes alkyl or cycloalkyl, but is not restricted to these radicals. Preferred xanthates are potassium $(C_1-C_4)$alkyl xanthates and sodium $(C_1-C_4)$alkyl xanthates.

Based on the state of the art, it was not to be expected that the process according to the invention yields the desired 2-mercaptobenzothiazoles in almost quantitative yield. Nucleophilic replacement of halogen atoms on aromatics usually only takes place if these are sufficiently activated by other electrophilic groups (for example $NO_2$). In contrast, the process according to the invention even leads to the desired result when other deactivating radicals (for example $CH_3$ or $OCH_3$) are present instead of activating substituents.

Both technical-grade xanthates, such as are widely commercially available as flotation auxiliaries, and freshly prepared xanthates, which can be produced in situ before or during the reaction from an alcohol, a strong base and carbon disulfide, are suitable for the reaction according to the invention. Sodium xanthates and potassium xanthates of lower alcohols are preferably used, but alkaline earth metal xanthates, such as calcium xanthate, are also possible. Sodium hydroxide solution or potassium hydroxide solution and methanol, ethanol, propanol, isopropanol, butanol or isobutanol are preferably used for the preparation of the former. Instead of using the base and alcohol separately, it is, of course, also possible to use the corresponding alkali metal alcoholates as the starting substances. The reaction with carbon disulfide can be carried out in the presence or absence of an alcohol, but it is necessary for a base to be present here. Suitable bases are, likewise, NaOH and KOH, and furthermore alkali metal carbonates and bicarbonates and alkaline earth metal carbonates and bicarbonates, such as $K_2CO_3$, $Na_2CO_3$, $NaHCO_3$ or $CaCO_3$. The molar ratio of the reactants is not critical and can be varied within wide limits for a suitable experimental arrangement. Thus, either more than or less than the molar amount of 2-halogenoanilines can be employed. If the aniline is employed in excess, it can be recovered during working up, by extraction with suitable solvents (for example toluene). However, molar ratios (xanthate or carbon disulfide:2-halogenoaniline) of 0.8:1 to 4:1, in particular 1:1 to 3:1, are preferred for economic reasons. In the case of reactions in the equimolar range, it is advantageous to add an auxiliary base to neutralize the 2-mercaptobenzothiazole formed, in order to achieve a high conversion of 2-halogenoaniline. Suitable bases are, for example, alkali metal carbonates, which are then employed in at least equivalent amounts. Since an excess of alkali metal carbonate has an advantageous effect on the yield, the preferred amount of alkali metal carbonate added is in the order of 0.5 mole to 4 moles per mole of halogenoaniline used.

The reaction temperature can be varied within wide limits. For practical reasons, a temperature is chosen in the range from about 80° C. to 250° C., the range from 100° C. to about 170° C. being preferred. It is expedient to carry out the process in the presence of a solvent. Suitable solvents are, above all, highboiling polar aprotic solvents, such as dimethylformamide, dimethylacetamide, N-methylpyrrolidone, dimethylsulfoxide or sulfolane. The reaction time depends on the conditions under which the process according to the invention is carried out. As a rule, it is between two and twenty-four hours.

The reaction is usually carried out under normal pressure, but it is also possible to carry it out in a closed reaction vessel, especially when free carbon disulfide is used. The pressure which builds up then depends on the chosen reaction temperature.

If desired, after the cyclization has been carried out, the 2-mercaptobenzothiazoles prepared by the process according to the invention are liberated from the salts originally obtained, by adding acids. For some subsequent reactions after the process according to the invention, it is not necessary to use free mercaptans; thus, for example, chlorinations, alkylations or oxidations can be carried out directly using the salts. The products can be worked up by distilling off the solvent and/or by adding water, before acidification. The free mercaptans are then isolated by filtration.

The 2-mercaptobenzothiazoles are suitable as reactive thiols for numerous purposes. They can be used, for example, as vulcanization auxiliaries or as starting substances for the preparation of dyestuffs, pharmaceuticals and plant protection agents (compare, for example, Japanese Preliminary Published Application No. 72/10,124, Japanese Preliminary Published Application No. 71/23,015, British Patent Specification No. 1,153,648, German Offenlegungsschrift No. 2,640,730 and German Offenlegungsschrift No. 2,531,427).

The following examples illustrate the process according to the invention:

EXAMPLE 1

(a) A solution of 216.2 g of sodium ethylxanthate in 250 ml of dimethylformamide is added dropwise to a solution, heated to 140°–150° C., of 63.8 g of 2-chloroaniline in 150 ml of dimethylformamide in the course of one hour, under a nitrogen atmosphere. During this addition, the internal temperature is kept at 150° C. by removing some of the distillate. The reaction mixture is then subsequently stirred under reflux for about 12 hours, cooled to about 80° C. and stirred into 1.2 l of ice-water. The resulting cloudy solution is acidified and the 2-mercaptobenzothiazole which has precipitated is filtered off. After washing and drying, 79 g (94.6% of theory) of 2-mercaptobenzothiazole of melting point 179°–180° C. are obtained.

(b) 6-Chloro-2-mercaptobenzothiazole (melting point: 260°–262° C.) is obtained in 95.6% yield in an analogous manner after a reaction time of 2½ hours.

The process conditions can be varied within wide limits, according to the following table: Explanations for the table:

TABLE 1

6-Chloro-2-mercaptobenzothiazole, prepared by reacting 2,4-dichloroaniline with xanthates

| Molar ratio aniline:xanthate | Xanthate [1] | S [2] | Addition of base | Reaction time (total) hours | Yield % | Melting point (°C.) |
|---|---|---|---|---|---|---|
| 1:3 | NaEx | DMSO | — | 4 | 93.7 | ~256 |
| 1:3 | NaEx | DMAA | — | 4 | 94.3 | 254–256 |
| 1:3 | NaEx | NMP | — | 4 | 91 | 257 |
| 1:3 | KEx | DMF | — | 3.5 | 95.2 | ~260 |
| 1:2 | NaIBX | DMF | 1 equivalent of $K_2CO_3$ | 20 | 96.3 | ~261 |
| 1:1.1 | NaIBX | DMF | 2 equivalents of $CaCO_3$ | 24 | 94.8 | ~258–260 |
| 1:1.2 | KIBX | DMF | 2.5 equivalents of $Na_2CO_3$ | 22 | 87.5 | ~257 |
| 1:3 | NaIPX | DMF | — | 4 | 92.8 | ~258 |
| 1:0.8 | | | | | | |

[1] NaEx = sodium ethyl xanthate
KEx = potassium ethyl xanthate
NaIBX = sodium isobutyl xanthate
NaIPX = sodium isopropyl xanthate
[2] S = solvent
DMSO = dimethylsulfoxide
DMAA = dimethylacetamide
NMP = N—methylpyrrolidone
DMF = dimethylformamide

EXAMPLE 2

(a) 205 g of carbon disulfide are added dropwise to a stirred suspension of 135 g of sodium methylate in 1.3 l of dimethylformamide, under a nitrogen atmosphere. During this addition, the temperature of the reaction mixture rises to about 70° C. A solution of 288 g of 2,4-dibromoaniline in 300 ml of dimethylformamide is added dropwise at an internal temperature of 70°–80° C. in the course of about 30–60 minutes. Thereafter, the internal temperature is increased to 100°, with good reflux cooling, and is maintained at this level for about 14 hours, and the reaction mixture is then cooled, stirred into 6 l of water and acidified. The 6-bromo-2-mercaptobenzothiazole which precipitates is filtered off and washed with water. After drying in vacuo, 272 g (96.3% of theory, relative to the 2,4-dibromoaniline employed) of 6-bromo-2-mercaptobenzothiazole are obtained in a purity sufficient for further reactions. A purified sample had a melting point of 278°.

(b) 5-Chloro-2-mercaptobenzothiazole (melting point: 191°–193° C.) is obtained in 93.5% yield in an analogous manner after a reaction lasting 17 hours, using 2,5-dichloroaniline.

(c) 5,6-Dichloro-2-mercaptobenzothiazole (melting point: 234°–236°) is obtained in 88% yield in an analogous manner, using 2,4,5-trichloroaniline.

(d) 6-Chloro-2-mercaptobenzothiazole (melting point: 257°–295°) is obtained in 91% yield in an analogous manner after a reaction lasting 16 hours, using 2,4-dichloroaniline.

EXAMPLE 3

(a) 91 g of carbon disulfide are added dropwise to a stirred suspension of 162 g of 2,4-dichloroaniline and 414 g of potassium carbonate in 1,000 ml of dimethylformamide at about 25°–30° C. in the course of 40 minutes, under a nitrogen atmosphere. The mixture is then warmed to an internal temperature of 150° C. in the course of 2 hours, and this temperature is maintained for 16 hours. The batch is cooled and filtered and the filtrate is largely freed from dimethylformamide. 600 ml of water are added to the residue which remains, the mixture is acidified and the product which precipitates is filtered off and dried. 187.6 g (93.2% of theory) of 6-chloro-2-mercaptobenzothiazole of melting point 258° C. are obtained.

(b) 6-Methyl-2-mercaptobenzothiazole (melting point: 179°–181°) is obtained in 90.7% yield in an analogous manner, using 2-chloro-4-methylaniline.

EXAMPLE 4

A solution of 250 g of potassium isobutyl xanthate (about 90% pure) in 400 ml of dimethylformamide is added dropwise to a mixture of 141.5 g of 2-chloro-6-methylaniline and 276 g of potassium carbonate in 1 liter of dimethylformamide at 150° C. in the course of one hour, under a nitrogen atmosphere. The reaction mixture is stirred for about a further 26 hours, whilst cooling intensively. The batch is cooled, freed from salt and then concentrated to dryness. The residue is taken up in 400 ml of water and the mixture is acidified. The 4-methyl-2-mercaptobenzothiazole which precipitates is filtered off, washed with water and dried. 172 g (95% of theory) of 4-methyl-2-mercaptobenzothiazole of melting point 188°–190° C. are obtained.

EXAMPLE 5

326 g (2 moles) of 2,4-dichloroaniline and 331 g (2.4 moles) of potassium carbonate in 1.5 liters of dimethylformamide are warmed to 150° C., under a nitrogen atmosphere, and a solution of 384 g of sodium ethyl xanthate (about 90% pure) in 600 ml of DMF is then added dropwise in the course of 1.5 hours. The mixture of DMF, ethanol and $CS_2$ which distills off is recycled continuously into the reaction mixture via a metering pump. After about 20 hours, $CS_2$ can no longer be detected in the distillate. The reaction mixture is cooled to about 60° C., freed from salt and concentrated in vacuo. The resulting residue is taken up in 4 liters of water and the mixture is acidified to pH 3–4. The 6-chloro-2-mercaptobenzothiazole which has precipitated is filtered off, washed with water and dried. Yield: 391 g (97% pure), melting point: 262°–265°.

When 182 g of $CS_2$ in ethanol was used (instead of Na ethyl xanthate) 381 g (94% of theory) of 6-chloro-2-mercaptobenzothiazole of melting point 260°–264° are obtained in an otherwise identical manner.

Some variations of the process according to the invention are summarized in the following Table 2 (Example 6):

TABLE 2

| Example No. | (R)$_n$ | Molar ratio aniline: xanthate | Xanthate [1] | S [2] | Addition of base | Reaction time (total) [hours] | Yield [%] | Melting point (°C.) |
|---|---|---|---|---|---|---|---|---|
| 6 a | H | 1:3 | NaIBX | DMSO | — | 12 | 95.2 | 179–181 |
| b | H | 1:2 | KIBX | DMAA | 1 equivalent of K$_2$CO$_3$ | 20 | 93.8 | 178–180 |
| c | 5-CH$_3$ | 1:3 | NaIBX | DMF | — | 16 | 91.2 | 173 |
| d | 5,6-DiCH$_3$ | 1:3 | NaEX | DMF | — | 22 | 92.6 | |
| e | 6-CH$_3$ | 1:1.2 | NaEX | DMF | 4 equivalents of K$_2$CO$_3$ | 20 | 96.2 | 179–181 |
| f | 6-F | 1:3 | NaEX | DMF | — | 16 | 92.5 | 226–228 |
| g | 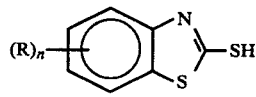 | 1:3 | NaEX | DMF | — | 18 | 87.6 | 165–167 |
| h | 6-C$_4$H$_9$-O- | 1:3 | NaEX | DMF | — | 20 | 84.5 | 156–157 |
| i | 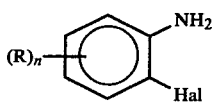 | 1:3 | NaEX | DMF | — | 20 | 78.5 | 208–212 |
| k | 5-H$_3$C—N⟨⟩N—SO$_2$— | 1:3 | NaEX | DMF | — | 14 | 96 | 250–252 |
| l | 5-CF$_3$ | 1:3 | NaIPX | DMSO | — | 12 | 92 | 208–210 |

[1] NaEX = sodium ethyl xanthate
KIBX = potassium isobutyl xanthate
[2] DMSO = dimethylsulfoxide
DMF = dimethylformamide
DMAA = dimethylacetamide

We claim:

1. A process for the preparation of a 2-mercaptobenzothiazole compound of the formula $$(R)_n{-}\text{benzothiazole-2-SH}$$

wherein
R is
(C$_1$–C$_4$) alkyl, (C$_1$–C$_4$) alkoxy,
(C$_1$–C$_4$) alkylthio, fluorine, chlorine, bromine, CF$_3$, NO$_2$, or CN, and
n is 0 or 1
which consists essentially of reacting a corresponding 2-halogenoanaline of the formula $$(R)_n{-}\text{C}_6\text{H}_3(\text{NH}_2)(\text{Hal})$$

wherein Hal is selected from the group consisting of fluorine, chlorine and bromine and R and n are as defined above with an alkali metal xanthate or alkaline earth metal xanthate at a temperature in the range of 100° C. to 170° C. and in the presence of a polar aprotic solvent.

2. The process of claim 1 wherein the 2-halogenoaniline and alkali metal xanthate or alkaline earth metal xanthate are reacted in the presence of a base selected from the group consisting of alkali metal hydroxide, alkali metal carbonate, alkaline earth metal carbonate, alkali metal bicarbonate, and alkaline earth metal bicarbonate.

3. The process of claim 2 wherein the base is potassium carbonate.

4. The process of claim 2 wherein the 2-halogenoaniline and alkali metal xanthate or alkali earth metal xanthate are reacted in the presence of a polar aprotic solvent selected from the group consisting of dimethylformamide, dimethylacetamide, N-methylpyrrolidone, dimethylsulfoxide and sulfolane.

5. The process of claim 1 wherein said alkali metal xanthate is potassium (C$_1$–C$_4$) alkyl xanthate or sodium (C$_1$–C$_4$) alkyl xanthate.

6. The process of claim 1 wherein said xanthate is formed in situ by reaction of carbon disulfide in the presence of a corresponding base selected from the group consisting of alkali metal hydroxide, alkali metal carbonate, alkaline earth metal carbonate, alkali metal bicarbonate and alkaline earth metal bicarbonate.

* * * * *